(12) United States Patent
Ahmadi

(10) Patent No.: US 12,324,546 B2
(45) Date of Patent: Jun. 10, 2025

(54) HAND DRYING SYSTEM

(71) Applicant: Saman Ahmadi, Houston, TX (US)

(72) Inventor: Saman Ahmadi, Houston, TX (US)

( * ) Notice: Subject to any disclaimer, the term of this patent is extended or adjusted under 35 U.S.C. 154(b) by 636 days.

(21) Appl. No.: 17/699,589

(22) Filed: Mar. 21, 2022

(65) Prior Publication Data

US 2022/0296053 A1    Sep. 22, 2022

Related U.S. Application Data

(60) Provisional application No. 63/200,679, filed on Mar. 22, 2021.

(51) Int. Cl.
    A47K 10/48     (2006.01)
    A61L 9/14      (2006.01)
    A61L 9/20      (2006.01)

(52) U.S. Cl.
    CPC ........... A47K 10/48 (2013.01); A61L 9/14 (2013.01); A61L 9/20 (2013.01)

(58) Field of Classification Search
    CPC ............ A47K 10/48; A47L 9/14; A47L 9/20
    USPC ........................................................ 34/191
    See application file for complete search history.

(56) References Cited

U.S. PATENT DOCUMENTS

| | | | | |
|---|---|---|---|---|
| 4,398,310 A | * | 8/1983 | Lienhard | A47K 10/48 4/628 |
| 4,898,713 A | * | 2/1990 | Picard | A61L 2/20 422/62 |
| 5,985,151 A | * | 11/1999 | Ahmadi | B01D 69/00 210/321.74 |
| 6,038,786 A | * | 3/2000 | Aisenberg | A47K 10/48 34/267 |

(Continued)

FOREIGN PATENT DOCUMENTS

| | | | | |
|---|---|---|---|---|
| CA | 2974133 A1 | * | 3/2018 | ............ A47K 10/48 |
| CA | 2833536 C | * | 1/2020 | ............ A47K 10/48 |

(Continued)

OTHER PUBLICATIONS

Bobrick, Ada Recessed Hand Dryer, https://www.bobrick/com/products/washroom-accessories/restroom-accessories-catalog/hand-dryers/product/b-3725/, known at least as early as Mar. 20, 2022, web page last accessed Aug. 31, 2022, 5 pgs.

(Continued)

*Primary Examiner* — Stephen M Gravini
(74) *Attorney, Agent, or Firm* — Womble Bond Dickinson (US) LLP

(57) ABSTRACT

A hand drying system includes a drying chamber, a drain assembly, an intake assembly, and an exhaust assembly. The drying chamber defines an opening that is sized to receive hands of a user into the drying chamber. The drain assembly is connected to a chamber drain and is configured to drain fluids from within the drying chamber. The intake assembly has an intake conduit and a blower fan. The blower fan is configured to draw air into the intake conduit through an intake inlet and flow the drawn air into the drying chamber via chamber inlets. The exhaust assembly includes an exhaust conduit and an exhaust fan. The exhaust fan is configured to draw chamber air into the exhaust conduit via an exhaust inlet in the drying chamber and reduce air exiting the drying chamber through the opening.

19 Claims, 3 Drawing Sheets

(56) References Cited

U.S. PATENT DOCUMENTS

| | | | |
|---|---|---|---|
| 6,431,189 B1 * | 8/2002 | Deibert | A61L 2/22 |
| | | | 604/289 |
| 7,946,055 B2 * | 5/2011 | Churchill | A47K 10/48 |
| | | | 34/224 |
| 7,971,368 B2 * | 7/2011 | Fukaya | A47K 10/48 |
| | | | 222/1 |
| 8,607,472 B2 * | 12/2013 | Ishii | A61L 9/22 |
| | | | 34/526 |
| 9,125,533 B2 | 9/2015 | Babikian | |
| 9,441,885 B2 * | 9/2016 | Bayley | F26B 21/12 |
| 9,700,183 B2 | 7/2017 | Babikian | |
| D818,647 S | 5/2018 | Babikian | |
| D819,275 S | 5/2018 | Babikian | |
| D822,402 S | 7/2018 | Babikian | |
| D892,407 S | 8/2020 | Muenzer et al. | |
| 10,786,124 B2 * | 9/2020 | Fujimura | A47K 10/48 |
| 11,896,171 B2 * | 2/2024 | Gallob | E03C 1/186 |
| 2022/0296053 A1 * | 9/2022 | Ahmadi | A61L 9/20 |

FOREIGN PATENT DOCUMENTS

| | | | | |
|---|---|---|---|---|
| JP | 4474483 B1 * | 6/2010 | | A47K 10/48 |
| WO | WO-2012135830 A1 * | 10/2012 | | A47K 1/04 |
| WO | WO-2013052616 A2 * | 4/2013 | | A47K 10/48 |

OTHER PUBLICATIONS

Dyson Airblade dB Hand Dryer, https://web.archive.org/web/20210404205735/https:/www.dyson.comcommerical/hand-dryers/airblade-db-nickel, known at least as early as Apr. 4, 2021, web page last accessed Aug. 31, 2022, 13 pgs.

* cited by examiner

HAND DRYING SYSTEM

CROSS-REFERENCE TO RELATED APPLICATIONS

This application claims the benefit of, and priority to, U.S. Provisional Patent Application Ser. No. 63/200,679, filed Mar. 22, 2021, the entire contents of which are hereby incorporated by reference.

TECHNICAL FIELD

The present disclosure relates to apparatuses, methods, and systems for hand drying and, more specifically, to those apparatuses, methods, and systems utilizing air as a drying medium.

BACKGROUND

Hand dryers are common in bathrooms for providing a means for drying hands. Hand dryers can use a variety of drying mediums to absorb or remove water from hands. For example, some common drying mediums are paper towels, cloth towels, and air.

Air is commonly used as a drying medium in communal bathrooms to provide a contactless or semi-contactless means for drying hands. The contactless or semi-contactless means for drying hands may be a preferred option for being environmentally friendly and for possibly reducing cross-contamination with other individuals using the hand dryer or in the environment around the dryer.

When air is used as a drying medium, the air is typically warmed to increase its capacity for absorbing water and to warm water on the hands to cause the water to evaporate. This heated air is typically blown into the bathroom such that the heated air with the water absorbed from the hands is recirculated within the bathroom.

Recirculating the warmed air with the water absorbed from the hands may aerosolize bacteria, viruses, or other contaminants from the hands into the air. In addition, the warmed air may undesirably spread odors within the bathroom.

SUMMARY

Applicant has recognized a need to address the aforementioned problems and has developed hand dryers with certain features, such as improved efficacy of hand drying, a reduction in the spread of contaminants from the hands, and/or reduction in the spread of odors within a bathroom.

In an embodiment of the present disclosure, a hand drying system includes a drying chamber, a drain assembly, an intake assembly, and an exhaust assembly. The drying chamber is defined by a top wall, a bottom wall, a back wall, two side walls, and an opening opposite the back wall. The opening is sized to receive hands of a user into the drying chamber. The bottom wall defines a chamber drain and the back wall defines an exhaust inlet. The top wall and each of the side walls define a chamber inlet. The drain assembly is connected to the chamber drain and is configured to drain fluids from within the drying chamber. The intake assembly has an intake conduit and a blower fan. The intake conduit defines an intake inlet. The blower fan is configured to draw air into the intake conduit through the intake inlet and flow the drawn air into the drying chamber via the chamber inlets. The exhaust assembly includes an exhaust conduit and an exhaust fan. The exhaust conduit is connected to the exhaust inlet. The exhaust fan is configured to draw chamber air into the exhaust conduit via the exhaust inlet and reduce air exiting the drying chamber through the opening.

In embodiments, the exhaust fan draws more air through the exhaust inlet than the blower fan flows into the drying chamber. The intake assembly may include a heating element disposed within the intake conduit and configured to warm air entering the drying chamber.

In some embodiments, the intake assembly includes a filter disposed within the intake conduit. The intake assembly may include a disinfection system downstream of the filter.

In another embodiment of the present disclosure, a hand drying system includes a drying chamber, a drain assembly, and an exhaust assembly. The drying chamber is defined at least partially by a bottom wall, a back wall, and an opening opposite the back wall. The opening is sized to receive hands of a user into the drying chamber. The bottom wall defines a chamber drain and the back wall defines an exhaust inlet. The drain assembly is connected to the chamber drain and is configured to drain fluids from within the drying chamber. The exhaust assembly is connected to the exhaust inlet and is configured to draw air from within the drying chamber and reduces air exiting the drying chamber through the opening.

In embodiments, the exhaust assembly includes an exhaust fan and an exhaust conduit. The exhaust conduit is in fluid connection with the exhaust inlet. The exhaust fan is configured to draw air into the exhaust conduit through the exhaust inlet and to flow the drawn air through an exhaust outlet. The exhaust outlet may be configured to exhaust air to an external environment.

In some embodiments, the hand drying system includes an intake assembly having an intake inlet and an intake conduit. The drying chamber may define at least one wall that defines a chamber inlet therethrough. The intake conduit may be fluidly connected to the intake inlet with the chamber inlet such that air drawn into the intake inlet flows into the drying chamber through the chamber inlet. The at least one wall includes a top wall opposite the bottom wall. Additionally or alternatively, the at least one wall includes a side wall that extends perpendicular from the back wall towards the opening.

In certain embodiments, the intake assembly may include a blower fan between the intake inlet and the chamber inlet. The blower fan may be configured to draw air into the intake inlet and flow the drawn air into the drying chamber via the chamber inlet. The exhaust assembly may include an exhaust fan and an exhaust conduit. The exhaust conduit in fluid connection with the exhaust inlet. The exhaust fan may be configured to draw air into the exhaust conduit through the exhaust inlet and to flow the drawn air through an exhaust outlet. The exhaust fan may draw more air through the exhaust inlet than the blower fan flows into the drying chamber.

In particular embodiments, the intake assembly includes a heating element that is disposed within the intake conduit and that is configured to warm air entering the drying chamber. The intake assembly may include a filter that is disposed within the intake conduit. The intake assembly may include a disinfection system downstream of the filter.

In another embodiment of the present disclosure, a method of drying hands with a drying system includes detecting an object within a drying chamber of the hand drying system, activating the hand drying system, ceasing detection of an object within the drying chamber, deactivating the drying system, and capturing liquids within the drying chamber in a drain assembly. Activating the hand drying system is in response to detecting the object includes emerging an exhaust fan to draw chamber air from within the drying chamber. Deactivating the drying system is in response to ceasing detecting an object within the drying chamber such that the exhaust fan is deenergized. Capturing the liquids within the drying chamber in a drawn assembly such that fluid is prevented from exiting the drying chamber via an opening through which the object is received.

In embodiments, activating the hand drying system includes energizing a blower fan to flow air into the drying chamber and deactivating the drying system includes deenergizing the blower fan. The method may include warming air entering the drying chamber. Capturing the liquids within the drying chamber in the drain assembly may include flowing the captured liquid into a plumbing system of a building.

In another embodiment of the present disclosure, a hand drying system includes a drying chamber, an intake assembly, and an exhaust assembly. The drying chamber configured to receive a hand of a user, the intake assembly configured to flow air into the drying chamber, and the exhaust assembly is configured to draw air from the drying chamber.

In embodiments, the hand drying system includes a drain assembly that is configured to drain fluids from the drying chamber. The exhaust assembly may be configured to draw more air from the drying chamber than the intake assembly flows into the drying chamber. The hand drying system may include a filter that is disposed within the intake assembly or the exhaust assembly and a controller. The controller may be configured to provide a signal to a system indicator of the filter needing replacement.

In certain embodiments, the intake assembly flows air into the drying chamber and the exhaust assembly draws air from the drying chamber at the same time as the intake assembly flows air into the drying chamber.

Further, to the extent consistent, any of the embodiments or aspects described herein may be used in conjunction with any or all of the other embodiments or aspects described herein.

BRIEF DESCRIPTION OF THE DRAWINGS

Various aspects of the present disclosure are described hereinbelow with reference to the drawings, which are incorporated in and constitute a part of this specification. Various embodiments as depicted in the accompanying drawings are for illustrative purposes, and should not be interpreted as limiting the scope of the embodiments. Furthermore, various features of different disclosed embodiments may be combined to form additional embodiments, which are part of this disclosure. In the drawings, like reference characters generally refer to the same parts throughout the different views. Also, the drawings are not necessarily to scale, emphasis instead being placed upon generally illustrating the various concepts discussed herein.

DETAILED DESCRIPTION

Figure 1:
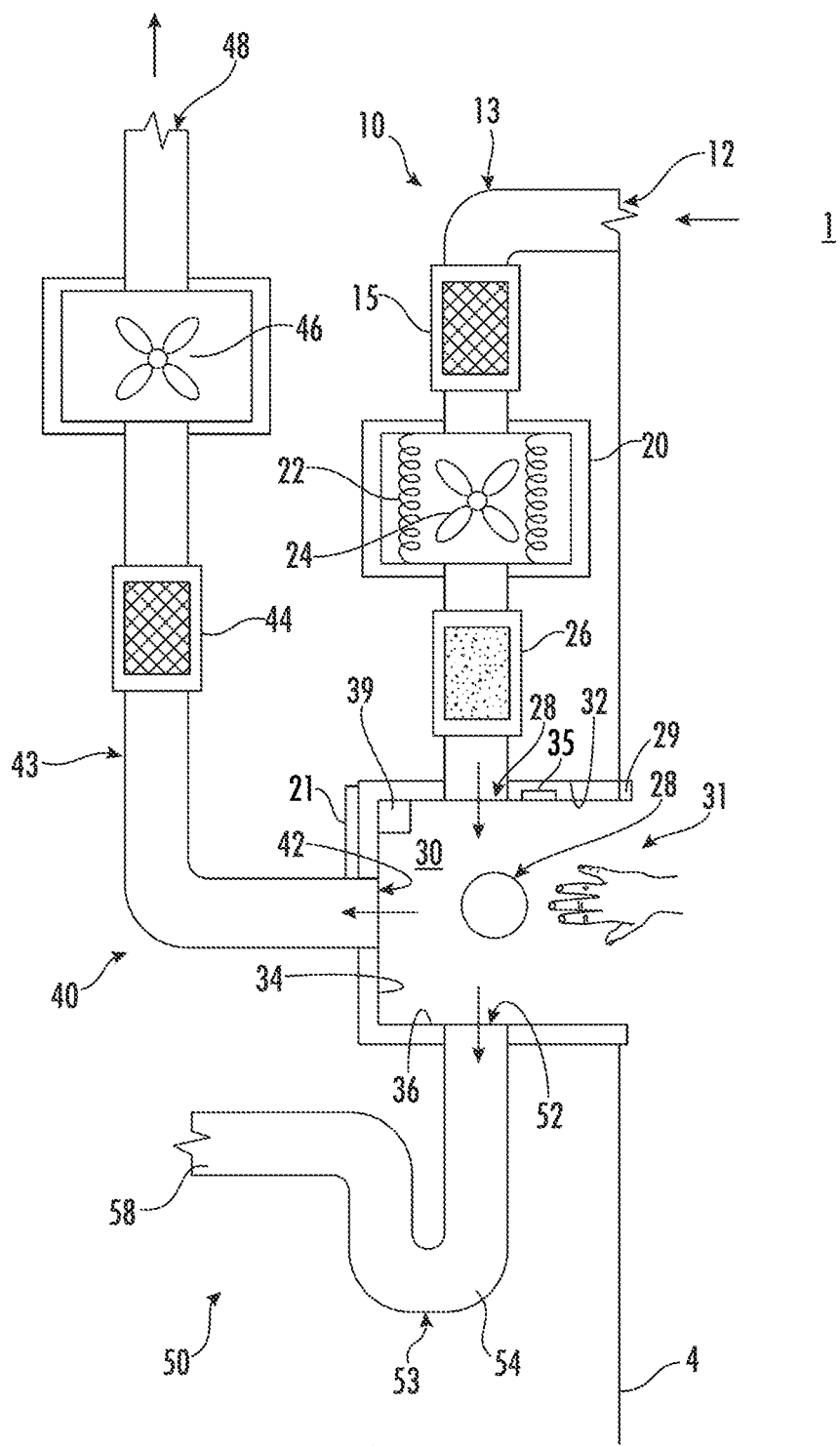
FIG. 1 is a schematic view of the hand drying system provided in accordance with an embodiment of the present disclosure.

The present disclosure will now be described more fully hereinafter with reference to example embodiments thereof with reference to the drawings in which like reference numerals designate identical or corresponding elements in each of the several views. These example embodiments are described so that this disclosure will be thorough and complete, and will fully convey the scope of the disclosure to those skilled in the art. Features from one embodiment or aspect can be combined with features from any other embodiment or aspect in any appropriate combination. For example, any individual or collective features of method aspects or embodiments can be applied to apparatus, method, product, or component aspects or embodiments and vice versa. The disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the," and the like include plural referents unless the context clearly dictates otherwise. In addition, while reference may be made herein to quantitative measures, values, geometric relationships or the like, unless otherwise stated, any one or more if not all of these may be absolute or approximate to account for acceptable variations that may occur, such as those due to manufacturing or engineering tolerances or the like.

Figure 2:
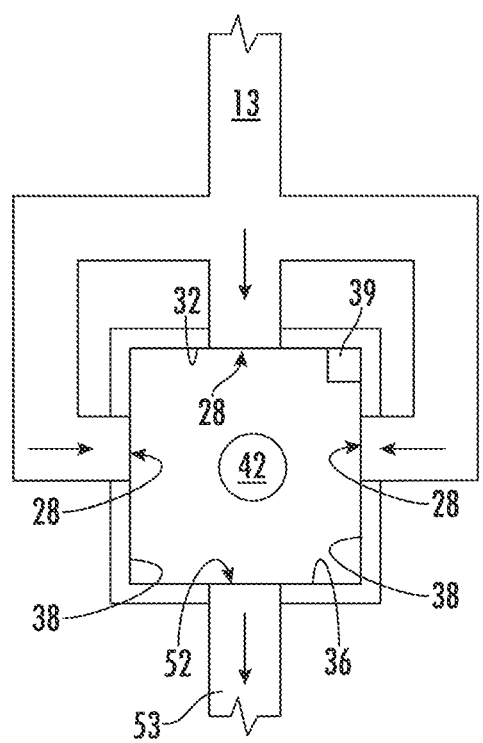
FIG. 2 is a front view of the hand drying system of FIG. 1.

Referring now to FIGS. 1 and 2, a hand drying system 1 is provided in accordance with an embodiment of the present disclosure. The hand drying system 1 is configured to draw air from the drying chamber 30 through an exhaust outlet 42 and drain water from the drying chamber 30. The hand drying system 1 may prevent air from the drying chamber 30 from being recirculated within a room including the hand drying system 1, e.g., a bathroom. The hand drying system 1 may include a drain 52 to remove water from within the drying chamber 30. In some embodiments, the hand drying system 1 is configured to blow air into a drying chamber 30 via one or more chamber inlets 28.

The hand drying system 1 includes a drying chamber 30, an exhaust assembly 40, and a drain assembly 50. The drying chamber 30 is defined substantially within a room wall 4 by a top wall 32, a back wall 34, a bottom wall 36, and side walls 38. The room wall 4 may be a full wall (e.g., a wall extending between a floor and ceiling); a partial wall such as a half wall, a pony or knee wall (e.g., a wall that does not extend fully between a floor and ceiling); or may be a hanging wall (e.g., a wall that extends partially between a floor and ceiling without terminating at either the floor or the ceiling).

The drying chamber 30 may be positioned a distance from a floor such that the drying chamber 30 is accessible for a majority of the public to insert their hands, including children. For example, the drying chamber 30 may be positioned between 36 inches and 60 inches from the floor, e.g., 48 inches. As detailed below, the walls defining the drying chamber 30 are substantially planar and form a cube. However, the walls defining the drying chamber 30 may be arcuate or curved and the drying chamber 30 may have other shapes including, but not limited to, a rectangular prism, an ovular prism, or spherical. The drying chamber 30 is sized to allow a user to insert and remove hands without contacting the walls defining the drying chamber 30 such that the hand dryer system 1 may be referred to as a touchless or contactless hand drying system. For example, when the drying chamber 30 has a cubic shape as shown, the drying chamber may have a width, height, and depth in a range of 6 inches to 15 inches, e.g., 12 inches.

The top wall 32, the bottom wall 36, and the side walls 38 define a receiving opening 31 opposite the back wall 34 that allows a user to insert hands into the drying chamber 30. The drying chamber 30 may be defined entirely within the room wall 4 such that the top wall 32, the bottom wall 36, and the side walls 38 terminate at the room wall 4. In some embodiments, a portion of the drying chamber 30 may extend beyond the room wall 4 such that one or more of the top wall 32, the bottom wall 36, or the side walls 38 extend beyond the room wall 4. The walls defining the receiving opening 31 (e.g., top wall 32, back wall 34, bottom wall 36, or side walls 38) may be formed of an anti-microbial material or may include an anti-microbial coating facing the drying chamber 30. Such an anti-microbial material or coating may reduce or eliminate bacteria or virus that contact the walls.

The exhaust assembly 40 is configured to draw air from within the drying chamber 30 and prevent or reduce the air from the drying chamber 30 from exiting through the opening 31. The exhaust assembly 40 may exhaust the air from the drying chamber to an exterior environment of a building. In some embodiments, the exhaust assembly 40 may filter or clean the air and exhaust the clean air back into the room or to an exterior environment. The exhaust assembly 40 includes an exhaust inlet 42, an exhaust fan 46, and an exhaust outlet 48 that are connected by a continuous conduit 43 that is suitable for flowing moist air therethrough, e.g., PVC tubing, stainless steel tubing, or sealed chambers within the room wall 4. The exhaust inlet 42 is defined in a back wall 34 of the drying chamber 30. The exhaust fan 46 is in fluid communication with the exhaust inlet 42 via the conduit 43 and is configured to draw air from the drying chamber 30 through the exhaust inlet 42.

The exhaust outlet 48 is configured to exhaust air drawn from the drying chamber 30. The exhaust outlet 48 may exhaust air to an external environment, may exhaust air into another room of a building, or may exhaust air back into a room including the room wall 4. The exhaust assembly 40 may include an exhaust filter 44 disposed within the conduit 43 to filter the air drawn from the drying chamber 30 before the drawn air is exhausted through the exhaust outlet 48. As shown, the exhaust filter 44 is disposed upstream of the exhaust fan 46; however, the exhaust filter 44 may be disposed downstream from the exhaust fan 46 and may be a HEPA rated filter. The exhaust assembly 40 may include another purification or disinfection assembly between the exhaust inlet 42 and the exhaust outlet 48. For example, the exhaust assembly may include an ionizer, an ozone disinfection assembly, or UV disinfection assembly.

The drain assembly 50 is configured to capture or drain liquids that drip from hands within the drying chamber 30 and flow the captured liquid out of the drying chamber 30. The drain assembly 50 includes a chamber drain 52 and a drain tube 53 that extends from the chamber drain 52 to a drain outlet 58. The drain outlet 58 may be connected to a plumbing system of a building to drain water from within the drain assembly 50. The drain assembly 50 may include a trap 54 to prevent gases from passing from the drain outlet 58 to the chamber drain 52 while allowing fluid to flow from the chamber drain 52 to the drain outlet 58. The bottom wall 36 may be shaped to promote flow of fluid into the chamber drain 52. For example, the bottom wall 36 may have a frustoconical shape, a dish shape, a bowl shape, a pyramid shape, or another suitable shape for guiding water or other liquids to the chamber drain 52. The drain assembly 50 may prevent or reduce liquids from contacting or flowing down the room wall 4. In some embodiments, the drain assembly 50 includes a trap primer to maintain water within the trap 54 or prevent the trap 54 from drying out.

Continuing to refer to FIG. 1, the hand drying system 1 may include an intake assembly 10 to provide and warm air entering the drying chamber 30. The intake assembly 10 includes an intake inlet 12, a blower assembly 20, and one or more chamber inlets 28. The intake inlet 12 is configured to draw air into the intake assembly 10. The intake inlet 12 may be positioned on the room wall 4 above the drying chamber 30 such that the intake inlet 12 draws air from the room including the hand drying system 1 or the intake inlet 12 may be positioned in a room remote to the room including the hand drying system 1. The drying chamber 30 may include a single chamber inlet 28 in the top wall 32 or one of the side walls 38. In some embodiments, the drying chamber 30 has a chamber inlet 28 in each of the side walls 38. In particular embodiments, the drying chamber 30 has a chamber inlet 28 in the top wall 32 and one of the side walls 38. In certain embodiments, the drying chamber 30 has a chamber inlet 28 in the top wall 32 and both of the side walls 38. The intake inlet 12 and the chamber inlets 28 are in fluid communication with one another via an intake conduit 13 that extends between the intake inlet 12 and the chamber inlets 28. The intake conduit 13 may include a split or a bridge adjacent the chamber inlets 28 such that a flow of air is split between the chamber inlets 28. The air may be split evenly or unevenly between the chamber inlets 28. The chamber inlets 28 may be positioned at a center point of each of the respective top wall 32 or side walls 38 or the chamber inlets 28 may be offset from a center point of the respective top wall 32 or side walls 38. The chamber inlets 28 may direct air in a direction orthogonal to the respective top wall 32 or side walls 38 or the chamber inlets 28 may direct air towards an opposing wall and the back wall 34 such that air flowing into the drying chamber 30 is at least partially directed towards the exhaust inlet 42.

The blower assembly 20 is configured to draw air into the intake inlet 12, flow air through the intake conduit 13, and flow air into the drying chamber 30 via the one or more chamber inlets 28. The blower assembly 20 includes a blower fan 24 that is configured to draw air in through the intake inlet 12 and flow air into the drying chamber 30 via the chamber inlets 28. The blower assembly 20 may include a heating element 22 that is configured to warm air flowing through the intake assembly 10. The heating element 22 may be disposed anywhere within the intake assembly 10. For example, the heating element 22 may be disposed about the blower fan 24, adjacent the intake inlet 12, adjacent the chamber inlets 28. The heating element 22 may be an electrical heating element or may be a liquid to air or air to air heat exchanger. The heating element 22 may be configured to warm air flowing through the intake assembly 10 to a temperature greater than ambient air. For example, the heating element 22 may warm air to a temperature in a range of 10° F. to 75° F. greater than ambient air or to a temperature in a range of 75° F. to 200° F.

The intake assembly 10 may include a filter 15 that is configured to filter air flowing through the intake conduit 13. The filter 15 may be disposed upstream or downstream of the fan 24 and may be a HEPA rated filter. The intake assembly 10 may include an ionizer disinfection system, ozone disinfection system, or a UV disinfection system 26 upstream or downstream of the fan 24. The disinfection system 26 may actively kill bacteria or virus flowing through the intake conduit 13 before entering the drying chamber 30.

The hand drying system 1 may be a contactless drying system and be activated when hands pass through the opening 31 and deactivated when hands are removed. To detect hands entering the drying chamber 30, the hand drying system 1 may include a sensor 39 disposed within or adjacent the drying chamber 30. The sensor 39 may be a motion sensor, a proximity sensor, or a curtain sensor. The hand drying system 1 may be activated when the sensor 39 detects hands entering the drying chamber 30 such that the fans, e.g., blower fan 24 and exhaust fan 46, and the heating element 22 are activated and may be deactivated when the sensor 39 ceases to detect hands within the drying chamber 30. The deactivation of the hand drying system 1 may be delayed a predetermined deactivation time after the sensor 39 ceases to detect hands within the drying chamber 30. The predetermined deactivation time may be in a range of 0 seconds to 10 seconds, e.g., 5 seconds. The predetermined deactivation time may account for hands entering and exiting the drying chamber 30 or to cycle air from within the drying chamber 30 between users. The sensor 39 may function as or be integrated into a switch to activate or provide power to the fans or the heating element 22.

The hand drying system 1 may include a chamber light 35 that is configured to illuminate the interior of the chamber 30 and/or the hands of a user disposed within the chamber 30. The chamber light 35 may be activated or turned on when the sensor 39 detects hands within the drying chamber 30. The chamber light 35 may be activated when hands are detected within the drying chamber 30 and may remain on for a predetermined time after hands are removed from within the chamber 30 or when hands are no longer sensed within the chamber 30. The predetermined time may be the same as the deactivation time of the rest of the hand drying system 1. As shown the chamber light 35 is positioned in the top wall 32 of the chamber 30. In some embodiments, the chamber light 35 may be positioned in other walls of the chamber 30 in addition to or alternatively from the top wall 32 to illuminate the hands of the user.

The hand drying system 1 may include a controller 21. The controller 21 may be disposed on the outside of the back wall 34 of the chamber 30 or may be disposed in other locations within the system 1, e.g., adjacent the blower assembly 20. The controller 21 may be in wired or wireless electrical or signal communication with other parts of the system 1. The controller 21 may be in electrical or signal communication with the sensor 39, the light 32, the blower assembly 20, and/or the exhaust assembly 40, e.g., the exhaust fan 46. The controller 21 may receive a signal from the sensor 39 when hands are detected within the chamber 30 and may activate the blower assembly 20, the exhaust assembly 40, and/or the chamber light 35 as detailed above.

In some embodiments, the controller 21 may be in communication with the filter 15 and/or filter 44. The controller 21 may provide an indication when the filter 15 or filter 44 are in need of replacement. The controller 21 may determine filter 15 or filter 44 are in need of replacement based on a pressure drop across the respective filter, an amount of time since replacement, an amount of air that has passed through the filter, an operating time of the blower assembly 20 or the exhaust assembly 40 since replacement of the respective filter, or a flow rate of air through the respective filter.

The hand drying system 1 may include an indicator light 29 to provide a status of the filter 15 and/or the filter 44. The indicator light 29 may be positioned on or in the chamber 30. The indicator light 29 may be inconspicuous to a user of the dryer system 1 or may be intentionally visible to a user. In some embodiments, the indicator light 29 may be positioned on the back wall 34 to be visible to a technician or maintenance personnel but not be seen by a user of the dryer system 1. In embodiments, the indicator light 29 may be positioned on the top wall 32 or the bottom wall 36 to be seen by a technician, maintenance personnel, and/or a user of the drying system 1. The indicator light 29 may be illuminated with a first color, e.g., green, when the filter 15 and/or filter 44 is functioning properly and a second color, e.g., yellow, when the filter 15 and/or filter 44 is not functioning properly or needs to be replaced. The indicator light 29 may be illuminated with the second color when the filter 15 is not functioning properly or needs to be replaced and third color, e.g., orange when the filter 44 is not functioning properly or needs to be replaced. In some embodiments, the indicator light 29 may be illuminated with a fourth color, e.g., red, when both the filter 15 and the filter 44 are not functioning properly or need to be replaced. In some embodiments, the indicator light 29 may also provide a status of other aspects of the hand drying system 1. For example, the indicator light 29 may provide a status of the disinfection system 26. In some embodiments, the indicator light 29 may illuminate in a color specific, e.g., purple, to indicate when the disinfection system 26 was functioning improperly and needed service.

In embodiments, the controller 21 may be in signal communication with systems outside of the hand drying system 1. The controller 21 may be in wired or wireless communication with systems outside of the hand drying system 1. In some embodiments, the controller 21 is in signal communication with systems of a facility or building, e.g., a building automation system. The controller 21 may provide signals to systems of the facility or building to provide a status of the hand drying system 1. For example, the controller 21 may provide a signal to systems of the facility or building when a component of the system needs maintenance or replacement, e.g., when the filter 15 or filter 44 needs to be maintained or replaced, when the disinfection system 26 needs maintenance, or fan 24 or fan 46 needs maintenance.

Figure 3:
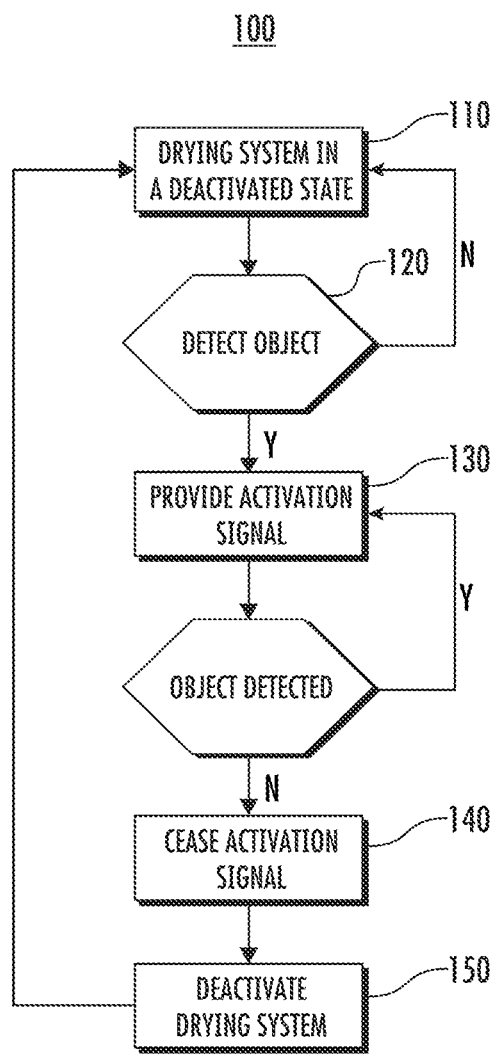
FIG. 3 is a flow chart of a method of drying hands in accordance with an embodiment of the present disclosure.

Referring to FIG. 3, a method 100 of drying hands is disclosed in accordance with an embodiment of the present disclosure with reference to the hand drying system 1 of FIGS. 1 and 2. The method 100 includes the hand drying system 1 being in a deactivated state (Step 110). In the deactivated state, the fan or fans, e.g., blower fan 24 and exhaust fan 46, of the hand drying system 1 are deenergized such that the fans are not circulating air through the hand drying system 1. In the deactivated state, the heating element 22 may be deenergized. In some embodiments, in the deactivated state, the heating element 22 is maintained at a predetermined temperature such that the heating element 22 warms air upon activation of the hand drying system 1. The predetermined temperature may be in a range of 75° F. and 200° F.

In the deactivated state, a sensor 39 of the hand drying system 1 is active to sense objects entering a drying chamber 30 of the hand drying system 1. When the sensor 39 detects an object such as a human hand entering the drying chamber 30 (Step 120), the sensor 39 provides an activation signal to activate the hand drying system 1 (Step 130). The sensor 39 may detect motion of objects or a position of objects. For example, the sensor 39 may be a motion sensor configured to detect movement within the drying chamber 30 or may be a curtain sensor that is configured to detect a break in a curtain disposed at the opening 31 of the drying chamber 30.

When the hand drying system 1 is activated, the fan or fans, e.g., blower fan 24 and exhaust fan 46, are energized to provide air into the drying chamber 30 and draw air out of the drying chamber 30, respectively. The exhaust fan 46 may be sized to flow a greater amount of air than the blower fan 24 such that air is drawn into the drying chamber 30 through chamber inlets 28 and the opening 31 of the drying chamber 30 such that air within the drying chamber 30 is prevented, or reduced, from returning to a room through the opening 31. Reducing or preventing air from returning to the room through the opening 31 may reduce contaminants, e.g., bacteria, virus, or dirt, within the room. In addition, as air is cycled through the drying chamber 30, water or other liquids may drip onto a bottom wall 36 of the drying chamber 30 and into the chamber drain 52. The water or other liquids may flow into the drain assembly 50.

The hand drying system 1 remains activated while the sensor 39 detects objects within the drying chamber 30. When the sensor 39 ceases to detect objects within the drying chamber 30, e.g., ceases to detect motion or an object passing through a curtain, the sensor 39 ceases to provide the activation signal (Step 140). When the sensor 39 ceases to provide the activation signal, the hand drying system 1 returns to the deactivated state (Step 150). The hand drying system 1 may return to the deactivated state immediately when the activation signal ceases or may remain activated for a predetermined amount of time before returning to the deactivated state. The predetermined amount of time may be in a range of 0 seconds to 10 seconds. The predetermined amount of time may allow for air within the drying chamber 30 to be cycled before another user places hands within the drying chamber 30. When the hand drying system 1 returns to the deactivated state, the sensor 39 remains active to detect another object entering the drying chamber 30 (Step 110).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A hand drying system comprising:
   a drying chamber defined by a top wall, a bottom wall, a back wall, two side walls, and an opening opposite the back wall, the opening sized to receive hands of a user into the drying chamber, the bottom wall defining a chamber drain, the back wall defining an exhaust inlet, the top wall and each of the side walls each define a chamber inlet;
   a drain assembly connected to the chamber drain and configured to drain fluids from within the drying chamber;
   an intake assembly having an intake conduit and a blower fan, the intake conduit defining an intake inlet, the blower fan configured to draw air into the intake conduit through the intake inlet and flow air into the drying chamber via the chamber inlets; and
   an exhaust assembly including an exhaust conduit and an exhaust fan, the exhaust conduit connected to the exhaust inlet, the exhaust fan configured to draw air from the drying chamber into the exhaust conduit via the exhaust inlet and reduce air exiting the drying chamber through the opening.

2. The hand drying system according to claim 1, wherein the exhaust fan draws more air through the exhaust inlet than the blower fan flows into the drying chamber.

3. The hand drying system according to claim 1, wherein the intake assembly includes a heating element disposed within the intake conduit and configured to warm air entering the drying chamber.

4. The hand drying system according to claim 1, wherein the intake assembly includes a filter disposed within the intake conduit.

5. The hand drying system according to claim 4, wherein the intake assembly includes a disinfection system downstream of the filter.

6. A hand drying system comprising:
   a drying chamber defined at least partially by a bottom wall, a back wall, and an opening opposite the back wall, the opening sized to receives hands of a user into the drying chamber, the bottom wall defining a chamber drain, the back wall defining an exhaust inlet;
   an intake assembly configured to discharge air into the drying chamber,
   a drain assembly connected to the chamber drain and configured to drain fluids from within the drying chamber; and
   an exhaust assembly separate from the intake assembly, the exhaust assembly connected to the exhaust inlet and configured to draw air from within the drying chamber and reduce air exiting the drying chamber through the opening.

7. The hand drying system according to claim 6, wherein exhaust assembly includes an exhaust fan and an exhaust conduit, the exhaust conduit in fluid connection with the exhaust inlet, the exhaust conduit extending from the exhaust inlet to an exhaust outlet such that the exhaust conduit is configured to direct all air from the exhaust inlet to the exhaust outlet, the exhaust fan configured to draw air into the exhaust conduit through the exhaust inlet and to flow air through the exhaust outlet.

8. The hand drying system according to claim 6, wherein the intake assembly comprises an intake inlet and an intake conduit, the drying chamber further defined by at least one wall including a chamber inlet defined therethrough, the intake conduit fluidly connecting the intake inlet with the chamber inlet such that air drawn into the intake inlet flows into the drying chamber through the chamber inlet.

9. The hand drying system according to claim 8, wherein the at least one wall includes a top wall opposite the bottom wall.

10. The hand drying system according to claim 9, wherein the at least one wall includes a side wall extending perpendicular from the back wall towards the opening.

11. The hand drying system according to claim 8, wherein the at least one wall includes a side wall extending perpendicular from the back wall towards the opening.

12. The hand drying system according to claim 8, wherein the intake assembly includes a blower fan between the intake inlet and the chamber inlet, the blower fan configured to draw air into the intake inlet and flow air into the drying chamber via the chamber inlet.

13. The hand drying system according to claim 12, wherein exhaust assembly includes an exhaust fan and an exhaust conduit, the exhaust conduit in fluid connection with the exhaust inlet, the exhaust fan configured to draw air into the exhaust conduit through the exhaust inlet and to flow air through an exhaust outlet, the exhaust fan drawing more air through the exhaust inlet than the blower fan flows into the drying chamber.

14. The hand drying system according to claim 8, wherein the intake assembly includes a heating element disposed within the intake conduit and configured to warm air entering the drying chamber.

15. The hand drying system according to claim 8, wherein the intake assembly includes a filter disposed within the intake conduit and a disinfection system downstream of the filter.

16. A hand drying system comprising:
   a drying chamber configured to receive a hand of a user;
   an intake assembly configured to flow air into the drying chamber from outside of the drying chamber; and
   an exhaust assembly separate from the intake assembly and configured to draw air from the drying chamber and discharge air to an external environment outside of the hand drying system.

17. The hand drying system according to claim 16, further comprising a drain assembly configured to drain fluids from the drying chamber.

18. The hand drying system according to claim 16, wherein the exhaust assembly is configured to draw more air from the drying chamber than the intake assembly flows into the drying chamber.

19. The hand drying system according to claim 16, further comprising a filter disposed within the intake assembly or the exhaust assembly and a controller, the controller configured to provide a signal to a system indicative of the filter needing replacement.

* * * * *